United States Patent
Gonopolskiy et al.

(10) Patent No.: US 8,452,358 B2
(45) Date of Patent: May 28, 2013

(54) OPTICAL-BASED PHYSIOLOGICAL SENSOR ASSEMBLY WITH DISPOSABLE BARRIER LAYER

(75) Inventors: Oleg Gonopolskiy, West Bloomfield, MI (US); Arik Anderson, Birmingham, MI (US); Ronald A. Widman, Macomb, MI (US)

(73) Assignee: Covidien LP, Mansfield, MA (US)

( * ) Notice: Subject to any disclaimer, the term of this patent is extended or adjusted under 35 U.S.C. 154(b) by 492 days.

(21) Appl. No.: 12/706,062

(22) Filed: Feb. 16, 2010

(65) Prior Publication Data

US 2010/0222654 A1   Sep. 2, 2010

Related U.S. Application Data

(60) Provisional application No. 61/156,645, filed on Mar. 2, 2009.

(51) Int. Cl.
*A61B 5/1455*   (2006.01)

(52) U.S. Cl.
USPC ............................................ 600/310; 600/344

(58) Field of Classification Search
USPC .................................................. 600/309–344
See application file for complete search history.

(56) References Cited

U.S. PATENT DOCUMENTS

| 5,054,488 A * | 10/1991 | Muz ............................. 600/344 |
| 5,217,013 A * | 6/1993 | Lewis et al. .................... 600/342 |
| 5,402,777 A * | 4/1995 | Warring et al. ................ 604/307 |
| 6,377,829 B1 * | 4/2002 | Al-Ali ........................... 600/323 |
| 2002/0111545 A1 * | 8/2002 | Lindberg et al. .............. 600/322 |

* cited by examiner

Primary Examiner — Eric Winakur
Assistant Examiner — Marjan Fardanesh

(57) ABSTRACT

A physiological sensor assembly includes a physiological sensor having at least one light source and at least one optical receiver. A substantially transparent barrier layer is disposed between the physiological sensor and the patient's skin such that the barrier layer is removably adhered to the physiological sensor and removably adhered to the patient's skin.

19 Claims, 3 Drawing Sheets

OPTICAL-BASED PHYSIOLOGICAL SENSOR ASSEMBLY WITH DISPOSABLE BARRIER LAYER

This application claims priority to U.S. Ser. No. 61/156,645 filed on Mar. 2, 2009, the contents of which are hereby incorporated by reference.

BACKGROUND

Non-invasive physiological sensing devices are used to elicit physiological information about a patient's body to help doctors diagnose, monitor, and treat medical conditions. Certain of such devices, including oximeters that measure the oxygen content in biological tissue, use well-known near-infrared spectroscopy (NIRS) techniques. Such devices commonly include a control/display unit and a sensor, where the sensor is connected to the control/display unit through a flexible cable. The sensor typically comprises a single-piece opaque planar pad that houses one or more light sources (e.g., light emitting diodes) for transmitting light into a patient's body and one or more optical receivers for receiving the light reflected from the patient's body. The sensor further includes electronic components, typically in the form of a printed circuit board, that communicate with and control the operation of the light sources and the optical receivers. The sensor generally has a pressure sensitive adhesive directly on the surface of the pad where the light sources and optical receivers are exposed so that the sensor can be affixed to the patient's body.

Known sensor pads typically are made from or include a layer of hydrophobic material, which makes the sensor pad occlusive (i.e., prevents or limits the passage of moisture vapor). The occlusive nature of the pad prevents the normal transport of moisture from the surface of the patient's skin, thereby preventing such moisture from passing through the sensor pad and into the sensor electronics. While it is important to protect the sensor electronics from moisture, the occlusive nature of the sensor pad can also lead to skin irritation and bacteria growth resulting from the build-up of moisture on the surface of the patient's skin under the sensor pad. This is a particular concern in neonates, where the initial cells die and exfoliate during a short duration to create new skin.

To prevent the build-up of moisture between a sensor pad and the patient's skin, it is a common practice for medical personnel to periodically remove the sensor from the patient's skin so that the area under the sensor can "breathe." But the sensors are typically configured to be one-time use devices and the repeated removal and replacement of the sensor tends to compromise the adhesive's ability to securely affix the sensor to the patient's body, which can degrade the quality of the data obtained by the sensor. Accordingly, in practice, medical personnel tend to dispose of the old sensor and replace it with a new sensor each time they remove it from the patient's body. However, this practice can be very costly and thus undesirable. Therefore, there is a need for a sensor usable with an NIRS sensing system that is readily reusable and that facilitates the evaporation of moisture from the surface of the patient's skin while still protecting the sensor electronics from moisture damage.

DETAILED DESCRIPTION

Disclosed herein below is a sensor assembly that facilitates re-use of a sensor and that also improves evaporation of moisture from the skin surface of a patient while still protecting the electronic components in the sensor from moisture damage. The sensor assembly includes a planar disposable near-infrared transparent barrier, such as a thin film, disposed between a near-infrared spectroscopy sensor (hereinafter, NIRS sensor) and the patient's skin. The planar barrier includes adhesive on one or both sides so that it can be removably affixed to the patient's skin and to the sensor. The barrier is a cost-effective way to permit a single sensor to be periodically applied, removed and re-applied to a patient's skin because a new disposable barrier (which is relatively inexpensive) can be applied between the patient's skin and the sensor for each re-application of the sensor. Further, the barrier is preferably non-occlusive so that moisture vapor is permitted to evaporate from the skin surface both when the sensor/barrier combination is affixed to the patient's skin and when the sensor is removed (but the barrier remains affixed to the patient). The barrier may also be supplied sterile to provide protection for the patient when a non-sterile sensor is placed in an area that is susceptible to infection.

Figure 1:
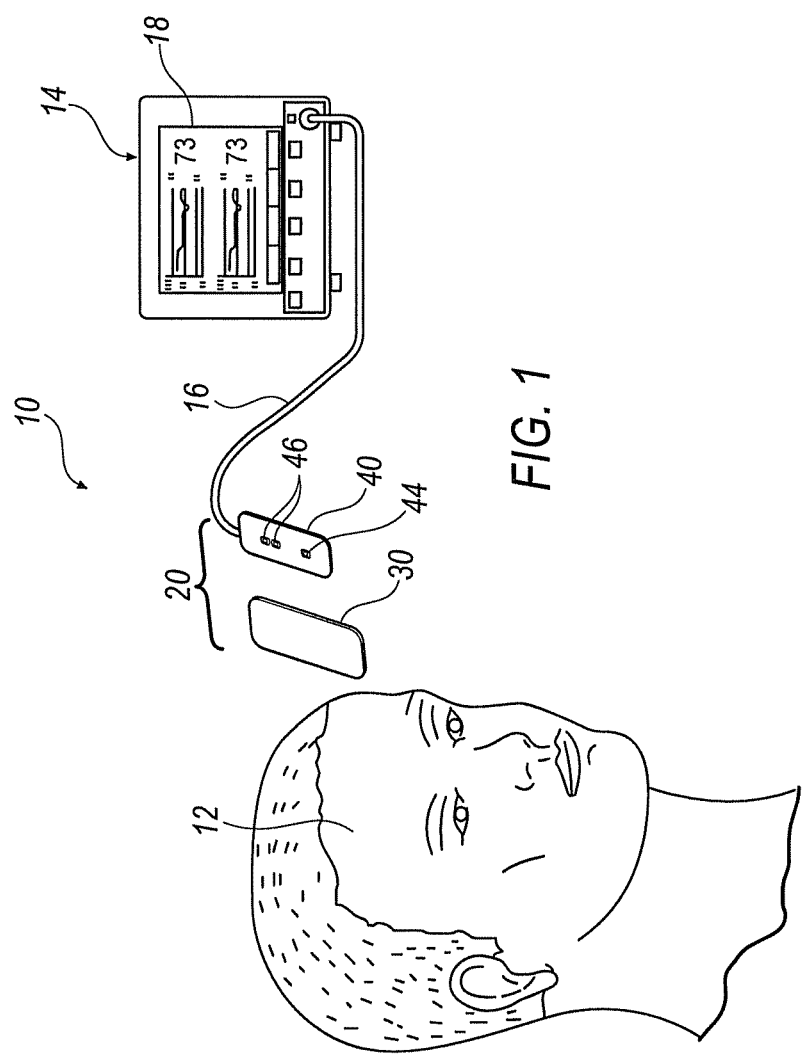
FIG. 1 illustrates an exploded view of an exemplary non-occlusive barrier sensor assembly positioned adjacent a patients tissue.
Figure 2:
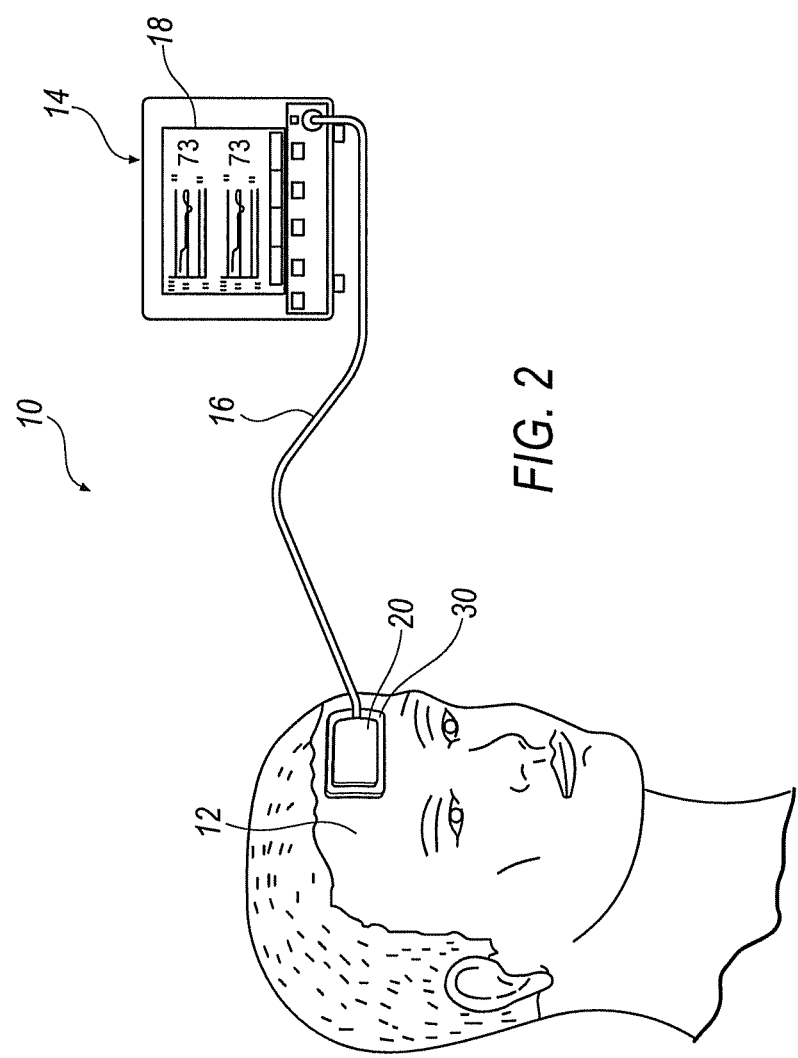
FIG. 2 illustrates an exemplary non-occlusive barrier sensor assembly positioned on a patient's skin and attached to a monitoring device.

FIGS. 1 and 2 illustrate an exemplary non-invasive physiological sensing system 10 according to one possible embodiment of the invention. FIG. 1 illustrates the system 10 in an "exploded" view, and FIG. 2 illustrates the system 10 assembled and affixed to the skin surface of a patient. In this particular embodiment illustrated in FIGS. 1 and 2, system 10 has a sensor assembly 20, which includes at least one planar barrier layer 30 and one NIRS sensor 40. In some embodiments, as shown in FIGS. 1 and 2, the barrier layer 30 is larger (has a greater surface area) than the sensor 40. The sensor assembly 20 is connected to and in signal communication with a control/display unit 14 through a flexible cable 16. The exemplary sensor 40 in FIGS. 1 and 2 includes one light source 44 (e.g., light emitting diode) and two optical receivers 46, though, in practice, the sensor 40 may include different numbers of light sources and optical receivers. The control/display unit 14 includes a display screen 18 to display physiological information of the patient. As shown in FIG. 2, the sensor assembly 20 is configured to be affixed to the surface of a patient's body, for example to a patient's forehead, with the barrier 30 being disposed between the patient's skin and the sensor 40. A person of ordinary skill in the art will recognize various other acceptable configurations of system 10. For example, sensor 40 may communicate with the control/display unit 14 wirelessly, eliminating the need for cable 16. Further, the sensor 40 may employ the use of fiber optic cables for communication. The sensor 40 may also use time resolved spectroscopy to examine the properties of the tissue and blood, Further, the sensor 40 may employ various combinations of light sources 44 and optical receivers 46 and comprise various shapes, configurations and degrees of flexibility to meet particular medical applications. Further, the barrier layer 30 may be various sizes relative to the size of the sensor 40. Further, sensor 40 may be affixed to other areas of the patient's body. The sensor 40 and control/display unit 14 may cooperate to measure and analyze various physiological features of a patient.

Figure 3:
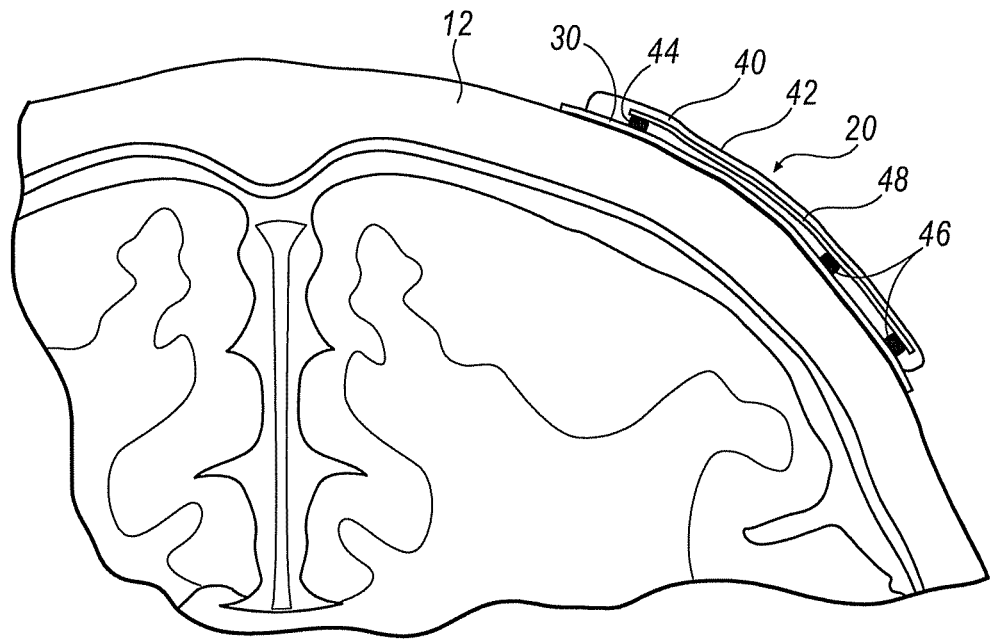
FIG. 3 illustrates an exemplary non-occlusive barrier sensor assembly positioned on a patient's skin.

FIG. 3 illustrates a detailed side sectioned view of the sensor assembly 20 positioned on a patient's skin 12, specifically a patient's skull. The sensor assembly 20 includes a sensor 40 and a barrier layer 30 affixed to both the sensor 40 and the patient's skin 12. The sensor 40 includes a sensor pad 42, which houses the light source 44 and the optical receivers 46. Printed circuit board 48 may also be housed within sensor pad 42 and is in electrical communication with the light source 44 and the optical receivers 46. Additionally, a wired sensor (not shown) may be housed within the sensor pad 42, eliminating the need for the printed circuit board 48. The wired sensor (not shown) may include a mechanical frame to hold the optical components 44, 46 and the electrical connections are made by point-to-point wiring. The barrier layer 30 has a surface area that is greater than the surface area of the sensor 40, which, if non-occlusive, facilitates some degree of moisture vapor evaporation from under the sensor 40, even when the sensor 40 is still affixed to the patient.

Figure 4:
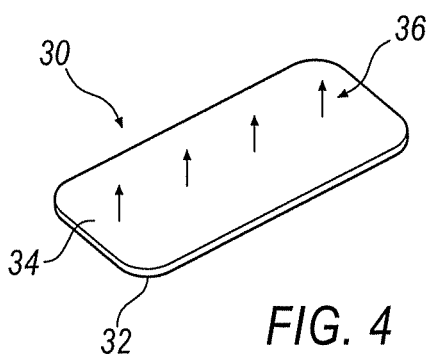
FIG. 4 illustrates an exemplary non-occlusive barrier.

FIG. 4 illustrates an exemplary embodiment of the barrier layer 30. The barrier layer 30 includes a first contact surface 32 and a second contact surface 34 on an opposing side. The first contact surface 32 is preferably coated with a first semi-permanent adhesive and the second contact surface 34 is preferably coated with a second semi-permanent adhesive, where the first adhesive has a greater adhesive strength than the second adhesive. In certain embodiments, the first surface 32 (with the stronger adhesive) is affixed to the patient's skin and the second surface 34 (with the weaker adhesive) is affixed to the sensor 40. This arrangement enables the sensor 40 to be relatively easily removed from the barrier layer 30 while the barrier layer 30 remains affixed to the patient's skin so that the sensor 40 can be later re-affixed to the still in-place barrier layer 30. In another embodiment, the second surface 34 may be provided without adhesive, in which case an adhesive applied to the sensor's 40 surface allows it to be affixed to the barrier layer 30. The adhesives are not limited to any specific type.

The barrier layer 30 is preferably non-occlusive i.e., permits moisture vapor from the surface of the patient's skin to pass therethrough (shown at element 36). This feature permits moisture vapor from the patient's skin to evaporate when the sensor 40 has been removed, even if the barrier layer 30 remains affixed to the patient's skin. Further, the barrier layer 30 permits some moisture to evaporate from the skin surface under the sensor 40, even when the sensor 40 is still affixed to the barrier layer 30, if the surface area of the barrier layer 30 is larger than the surface area of the sensor 40. The barrier layer 30 can be sterilized or provided sterile to protect areas that need to remain microbe-free, such as near a wound, over immuno-compromised skin, or in the sterile field of an operative site.

The barrier layer 30 may include an identifier that contains information about the time of use of the barrier layer 30. This allows a caregiver to use the identifier in order to change or move the barrier 30 to different location when a predetermined time has expired. Such identifier can be simply an area of the barrier 30 that can be tagged manually with a human readable mark of the time of barrier application. Further, the barrier 30 can include an radio frequency identification (RFID) tag that is readable by the Oximeter. Further, the RFID tag can automatically count time of application of the barrier.

The barrier layer 30 is substantially transparent to near-infrared, infrared and may be transparent to visible light so as to permit light emitted by the light source 44 to pass therethrough and into the body of the patient and for the reflected light signals to be received by the optical receivers 46. Transparency for visible light, in addition permits, examination of the tissue under the sensors 44, 46. Further, to minimize any signal error introduced by the barrier layer 30, it is preferable that the mean light path distance through the barrier layer 30 is substantially less than the mean light path distance in the patient's body. Therefore, in some embodiments, the thickness of the barrier layer 30 is preferably about 2 mm or less. Further, in some embodiments it is preferable that the light absorption coefficient of the barrier layer 30 is more than the light absorption coefficient of human tissue and/or the light scattering coefficient of the barrier layer 30 is more than the light scattering coefficient of human tissue. Further, to avoid undesirable guided light propagation (i.e., light piping) inside the barrier layer 30, it is preferable that the barrier layer 30 have a refractive index between approximately 1.0 and 1.5 and most preferably between about 1.0 and 1.33, which are the refractive indices of human tissue and water, respectively. Exemplary materials suitable for the barrier layer 30 are commercially-available under the trademarks Mepitel®, Mepitac® and Tegaderm™.

Figure 5:
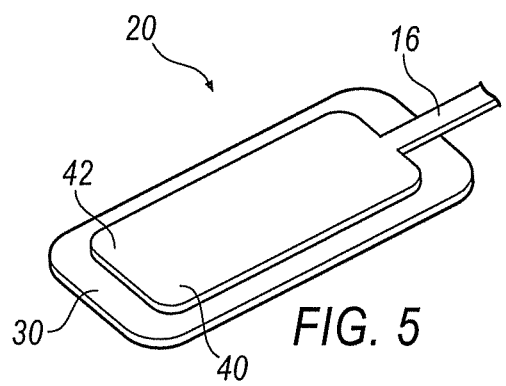
FIG. 5 illustrates an exemplary sensor assembly including a barrier layer affixed to an NIRS sensor.

FIG. 5 illustrates the sensor assembly 20, including sensor 40 and barrier layer 30, in isolation. The sensor assembly 20 shown in FIG. 5 illustrates the barrier layer 30 having a larger surface area than the sensor 40, which, in some embodiments where the barrier layer 30 is non-occlusive, is preferable so as to permit moisture vapor to evaporate from the patient's skin, even when the sensor 40 is still affixed to the patient's skin. This is due to fact that moisture vapor that would otherwise be trapped under the sensor 40 can pass through the barrier layer 30 and out of the barrier layer 30 from the surface area that extends beyond the outer borders of the sensor 40.

An exemplary use of the disclosed physiological sensing device is as follows. A medical personnel may affix a barrier layer 30 to a patient and then affix the sensor 40 to the barrier layer 30. Once assembled in this manner, the medical personnel may initiate the control/display unit 14 to cause the light source 44 to irradiate the patient's body, and the optical receivers 46 would receive return optical signals, which would be processed by the control/display unit 14 to generate physiological information. If the barrier layer 30 is non-occlusive and larger than the sensor 40, some degree of moisture will pass through the barrier layer 30 and evaporate while the sensor 40 is in place. When desirable, the medical personnel may remove the sensor 40 from the barrier layer 30 and patient. The medical personnel may leave the barrier layer 30 in place on the patient or may remove the barrier layer 30 from the patient. When it is desirable at a later time, the medical personnel can re-affix the sensor 40 to the patient, either by re-affixing it to first barrier layer 30 or disposing of the first barrier layer 30 and applying a new barrier layer 30. In this way, the sensor 40 is re-useable for the same patient, and, at most, the barrier layer 30, which is relatively inexpensive, may be disposed of between uses.

It is to be understood that the above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

What is claimed is:

1. A physiological sensor assembly, comprising:
   a physiological sensor having at least one light source and at least one optical receiver; and
   a substantially transparent to near infrared light barrier layer having a first surface and an opposing second surface, said first surface configured to removably adhere to a patient's skin and said second surface configured to removably adhere to the sensor,
   wherein said barrier layer is configured to allow moisture from the patient's skin to pass through the second surface when said sensor is disposed on said barrier layer.

2. The physiological sensor assembly of claim 1, wherein said adhesion to said skin is configured to be stronger than said adhesion to said sensor.

3. The physiological sensor assembly of claim 1, wherein said adhesion to said sensor is configured to be stronger than said adhesion to said skin.

4. The physiological sensor assembly of claim 1, wherein said barrier is non-occlusive.

5. The physiological sensor assembly of claim 3, wherein a surface area of said barrier layer is larger than a surface area of said sensor.

6. The physiological sensor assembly of claim 1, wherein said barrier has a refractive index between approximately 1.0 and approximately 1.5.

7. The physiological sensor assembly of claim 1, wherein said barrier has a thickness of approximately 2 millimeters or less.

8. The physiological sensor assembly of claim 1, wherein said barrier is sterilizable or supplied sterile to isolate a non-sterile sensor from the patient's skin.

9. A physiological sensing system, comprising:
   a physiological sensor having at least one near-infra red light source and at least one optical receiver;
   a controller/display unit in signal communication with said physiological sensor; and
   a substantially transparent, non-occlusive film that is removably affixed to said physiological sensor and removably affixed to a patient's skin;
   wherein said film has a surface area larger than a surface area of said physiological sensor to allow moisture from the patient's skin to pass through a surface of said film opposite the patient's skin when said film is adhered to said patient's skin and said sensor is adhered to said film.

10. The physiological sensing system of claim 9, wherein said film has a thickness of about 2 mm or less.

11. The physiological sensing system of claim 9, wherein said film has a refractive index between approximately 1.0 and approximately 1.5.

12. The physiological sensing system of claim 9, wherein said film is more strongly affixed to said patient's skin than to the physiological sensor.

13. The physiological sensing system of claim 9, wherein said film is more strongly affixed to said physiological sensor than to said patient's skin.

14. The physiological sensor assembly of claim 9, wherein said barrier is sterilizable to isolate a non-sterile sensor from the patient's skin.

15. The physiological sensor assembly of claim 9, wherein said barrier is supplied sterile to isolate a non-sterile sensor from the patient's skin.

16. A physiological sensor comprising:
   a sensor pad;
   at least one light source disposed on the sensor pad;
   at least one optical receiver disposed on the sensor pad and configured to detect light emitted by the at least one light source; and
   a non-occlusive barrier layer having a first surface and an opposing second surface, said first surface configured to removably adhere to a patient's skin and said second surface configured to removably adhere to the sensor pad, and wherein said barrier layer is configured to allow moisture from the patient's skin to pass through the second surface of the barrier layer when the barrier layer is adhered to the patient's skin and sensor pad is adhered to the barrier layer.

17. The physiological sensor of claim 16, wherein a surface area of said barrier layer is larger than a surface area of said sensor pad.

18. The physiological sensor of claim 16, wherein said adhesion to said skin is configured to be stronger than said adhesion to said sensor.

19. The physiological sensor of claim 16, wherein said adhesion to said sensor is configured to be stronger than said adhesion to said skin.

* * * * *